(12) United States Patent
Kupperblatt et al.

(10) Patent No.: US 6,702,803 B2
(45) Date of Patent: Mar. 9, 2004

(54) MULTI-STEP DRUG DOSAGE FORMS

(75) Inventors: Gary Kupperblatt, Hillsborough, NJ (US); Marc S. Karetny, Langhorne, PA (US); Ramaswamy Murari, Hillsborough, NJ (US); Suggy S. Chrai, Cranbury, NJ (US)

(73) Assignee: Delsys Pharmaceutical Corporation, Monmouth Junction, NJ (US)

( * ) Notice: Subject to any disclaimer, the term of this patent is extended or adjusted under 35 U.S.C. 154(b) by 0 days.

(21) Appl. No.: 09/766,695

(22) Filed: Jan. 22, 2001

(65) Prior Publication Data

US 2002/0072735 A1 Jun. 13, 2002

Related U.S. Application Data

(60) Provisional application No. 60/177,230, filed on Jan. 20, 2000.

(51) Int. Cl.$^7$ .............................. A61K 9/24; A61K 9/00; A61K 9/20; A61K 9/22
(52) U.S. Cl. .................... 604/890.1; 424/472; 424/473; 424/400; 424/464; 424/465; 424/468
(58) Field of Search .................. 424/473, 400, 424/472, 464, 465, 468; 604/890.1

(56) References Cited

U.S. PATENT DOCUMENTS

| | | | |
|---|---|---|---|
| 4,451,260 A | | 5/1984 | Mitra |
| 4,723,958 A | | 2/1988 | Pope et al. |
| 4,891,223 A | | 1/1990 | Ambegaonkar et al. |
| 5,017,381 A | * | 5/1991 | Maruyama et al. |
| 5,938,654 A | * | 8/1999 | Wong et al. |

FOREIGN PATENT DOCUMENTS

WO     WO 01/12103 A1     2/2001

* cited by examiner

Primary Examiner—Thurman K. Page
Assistant Examiner—Simon J. Oh
(74) Attorney, Agent, or Firm—Dechert LLP

(57) ABSTRACT

Controlled release, multi-step drug dosage forms comprising a plurality of dose units and a plurality of separators that control release of drug from the dose units. In one embodiment, a dose unit is a single dosage amount of a drug that is electrostatically deposited onto a substrate. The dosage forms are designed to deliver a drug to exhibit a desired pharmacokinetic profile.

25 Claims, 6 Drawing Sheets

MULTI-STEP DRUG DOSAGE FORMS

STATEMENT OF RELATED APPLICATIONS

This application claims priority of Provisional Application No. 60/177,230 filed Jan. 20, 2000.

FIELD OF THE INVENTION

The invention relates to controlled-delivery drug dosage forms. More specifically, the invention relates to multi-step drug dosage forms having an extended release component.

BACKGROUND OF THE INVENTION

First order release of a drug results from administration of medication as a single dose with the immediate release of a single dose unit. First order release is often undesirable, as in the case of drugs that have a wide therapeutic window or whose duration of action is shorter than the desired therapeutic duration. Zero order release, where the drug plasma concentration is nearly constant for an extended time, frequently requires continuous administration of the drug.

In many cases, the ideal release profile for an extended release dosage form is zero order drug release (i.e., the release of drug is independent of time, over a certain length of time). In the case of most extended release dosage forms, however, as the drug level inside the dosage form decreases, the rate of release also decreases. Consequently, dosage forms often show two phases of drug release: an initial phase, which may or may not be linear, and a second phase, which reflects the rapid depletion of the drug from the device. It would be advantageous to have a dosage form that exhibits a zero order release over substantially the entire period of drug release. Multi-step release systems have been proposed to achieve such profiles in that multi-step drug release permits an approximation to zero order drug delivery using a series of small doses.

Several U.S. patents describe multi-step, extended release oral dosage forms. Many of these patents rely on a mechanical release mechanism, wherein a driving means slidably moves dosage units within a housing until each is released from one end of the housing into the environment. The driving means is typically a fluid activated driving means such as a material in one end of the dosage form that swells upon contact with fluid. The release of drug is thus osmotically driven. One disadvantage of these types of devices is that they are essentially mechanical devices and can malfunction. Another disadvantage is that the device design is fairly inflexible because, among any other reasons, the choice of materials that can be used for the fluid activated swelling means is limited. Still another disadvantage is that such devices typically include a semi-permeable membrane through which fluid enters the device. On the other end of the device is an orifice or a larger opening. Blockage or other impediment of this opening would restrict the drug release and have a negative impact on drug delivery.

Many prior art multi-step devices include the drug in a conventional format (e.g., in a matrix or tablet form) and so have the disadvantages inherent in such formats. In particular, conventional processes for manufacturing tablets or capsules typically have many independent steps and often require several days or weeks to produce a product. The traditional processes for manufacturing tablets typically involve blending the bulk drug substance with excipients such as bulking agents, disintegrants, solubilizers, and flavors. After blending, the mixture is usually granulated, which frequently involves the addition of a liquid, before it is dried, milled, blended with lubricant, and compressed into a tablet prior to coating and packaging. Each step in these traditional processes requires investment in equipment, facilities, and labor. Process controls for each step must be established, dictating numerous in-process quality control checks. Because conventional quality control involves destructive testing of the product, only a small sample of the lot can be tested.

The art would therefore benefit from improved multi-step drug dosage forms, and a method for making them.

SUMMARY OF THE INVENTION

The illustrative embodiments of the present invention are directed to controlled release drug dosage forms that can be designed to deliver a drug at a desired pharmacokinetic profile. Some dosage forms in accordance with the illustrative embodiment of the present invention employ a plurality of dose units. In one embodiment, a dose unit is a single dosage amount of a drug that is disposed on a substrate, referred to herein as a "deposit". The dose units are assembled into controlled release multi-step dosage forms. In some embodiments, controlled release is achieved through the use of various structural elements such as substrates and separators, having various dissolution and/or drug release characteristics. A release profile desired for a particular drug can be achieved using a dosage form incorporating structural elements having dissolution and/or release characteristics to achieve the desired profile.

In some embodiments, a plurality of dose units are assembled into a dosage form. One or more separators are included to controllably and sequentially expose the dose units to the environment and allow release of drug from the dosage form. Release of drug can also be controlled by selection of the substrate for the dose unit, if one is used, and by the use of one or more overwrappings. The multi-layer construction of the dosage form and the manner in which the different layers are assembled allows the incorporation of multiple release-determining factors into the dosage form, such as different amounts of a drug, different drugs, and/or different materials that can impart different properties. Controlled release dosage forms can be assembled having the desired drug release profile, including immediate release as well as extended release from a single dosage form, to obtain a desired pharmacokinetic profile. The dosage form can be designed to exhibit a zero order release profile. Furthermore, the dosage form is advantageously designed to exhibit desired characteristics such as stability, reproducibility, precision, and safety, offering significant improvements over existing products that require multiple administrations per day to achieve similar profiles.

In some embodiments, the deposits are made using an electrostatic deposition process, which permits the manufacture of small, precisely controlled dose units. Electrostatic deposition can rapidly and accurately deposit pure drug on a substrate, which can greatly reduce the amount of time required to produce a batch. Less equipment and fewer operators are necessary, which can lower manufacturing cost. Each dose can be inspected with a non-destructive technique so that 100% inspection can be achieved. The elimination of off-line in-process quality checks can reduce product and lab material consumption.

DETAILED DESCRIPTION

Definitions

Figure 1:
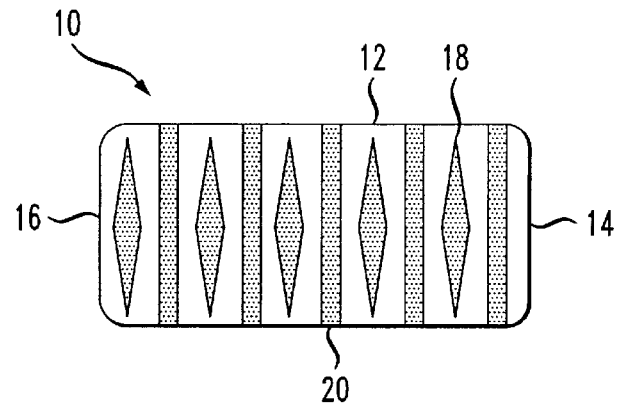
FIG. 1 depicts a first dosage form in accordance with the illustrative embodiment of the present invention.

The terms "active agent", "pharmaceutical" and "drug" are used interchangeably herein and are defined, for the purposes of this specification, as a compound, composition of matter, or mixture thereof that can be delivered from the system to produce a beneficial or useful result, such as the mitigation, diagnosis, cure, treatment, or prevention of a disease. This includes, in particular, any physiologically or pharmacologically active substance that produces a localized or systemic effect or effects in animals. This also includes diagnostic and prophylactic agents.

The term "controlled release" is defined, for the purposes of this specification, as a release of drug from a dosage form in a pre-determined manner.

The term "delayed release" is defined, for the purposes of this specification, as a release of drug at a time later than immediately after administration.

The term "deposit" is defined, for the purposes of this specification, as a single dose unit of drug held on a substrate.

The terms "deposition film," "deposition substrate" and "substrate" are used interchangeably herein and are defined, for the purposes of this specification, as a material upon which a dose unit is placed in forming a deposit.

The term "dissolve" is defined, for the purposes of this specification, as true dissolution, enzymatic degradation, bacterial digestion, erosion, and any other form of material breakdown, and these terms are used synonymously.

The term "dosage amount" is defined, for the purposes of this specification, as an amount of drug needed to achieve a desired beneficial or useful effect.

The term "dosage form" is defined, for the purposes of this specification, as a formulation of a drug or drugs in a form administrable to an animal, wherein the term animal is intended to encompass a human. While the illustrative embodiment of the invention has been described primarily as being directed to oral dosage forms such as tablets, capsules, and caplets, it is also applicable to dosage forms intended for other types of administration, such as, for example, vaginal and rectal suppositories, and implants.

The term "dose unit" is defined, for the purposes of this specification, as an isolated quantity of drug. In some embodiments, a dose unit includes a single dosage amount of the drug; in other embodiments, a dose unit includes more or less than a dosage amount. In some embodiments in which less than a dosage amount is included in a dose unit, two or more dose units are released at a time, as described further later in this specification.

The term "extended release" is defined, for the purposes of this specification, as a release of drug from a dosage form over an extended period of time. Extended release dosage forms allow a reduction in dosing frequency as compared to when the drug is presented in an immediate release dosage form.

The term "hydrophobic drug" is defined, for the purposes of this specification, as a drug that ranges from "sparingly soluble" to "practically insoluble or insoluble," as follows:

| Descriptive Term | Parts of Solvent Required for 1 Part of Solute |
| --- | --- |
| Sparingly soluble | from 30 to 100 |
| Slightly soluble | from 100 to 1000 |
| Very slightly soluble | from 1000 to 10,000 |
| Practically insoluble, or insoluble | 10,000 and over |

The term "immediate release" is defined, for the purposes of this specification, as a release of drug from a dosage form in a relatively brief period of time, generally up to about 60 minutes.

The term "modified release" is defined, for the purposes of this specification, to include delayed release, extended release, and pulsed release.

The term "pharmaceutically acceptable" is defined, for the purposes of this specification, to mean that the drug, etc., can be introduced safely into the human or animal body, for example, taken orally and digested.

The term "pulsed release" is defined, for the purposes of this specification, as a series of releases of drug from a dosage form.

The term "release mechanism" is defined, for the purposes of this specification, as a process by which drug is released from the dosage form.

The term "surfactant" is defined, for the purposes of this specification, as a surface active agent that displays wetting, detergent or soap-like qualities as those agents are understood by those skilled in the art. The term "surfactant" therefore includes ionic and nonionic surfactants or wetting agents commonly used in the formulation of pharmaceuticals, such as ethoxylated castor oil, benzalkonium chloride, polyglycolyzed glycerides, acetylated monoglycerides, sorbitan fatty acid esters, poloxamers, polyoxyethylene fatty acid esters, polyoxyethylene derivatives, monoglycerides or ethoxylated derivatives thereof, diglycerides or polyoxyethylene derivatives thereof, sodium docusate, sodium lauryl sulfate, magnesium lauryl sulfate, triethanolamine, cetrimide, sucrose laurate and other sucrose esters, glucose (dextrose) esters, simethicone, ocoxynol, dioctyl sodium sulfosuccinate, polyglycolyzed glycerides, sodium dodecylbenzene sulfonate, dialkyl sodium sulfosuccinate, fatty alcohols such as lauryl, cetyl and streryl, glycerylesters, cholic acid or derivatives thereof, lecithins and phospholipids.

The illustrative embodiment of the present invention comprises controlled release multi-step dosage forms and methods for making the dosage forms. The dosage forms are preferably orally administrable, and include an extended release portion.

In some embodiments, the dosage forms include a plurality of dose units in a single dosage form. The dosage forms further advantageously include a plurality of separators that control exposure of the dose units to the environment and thus release of the drug from the dosage form. In some embodiments, the dosage form includes one or more overwrappings, and/or other structural elements, that provide structural integrity to the dosage form and, optionally, to contribute to drug release characteristics.

The primary drug-release mechanism is dissolution of the separators. In some embodiments, secondary release mechanisms, including, without limitation, dissolution of overwrappings, dissolution of the deposit substrate, dissolution of the cover, and diffusion or other release of drug from a dose unit.

In some embodiments, a dose unit includes the drug in solid form, preferably in powder form. In other embodiments, a dose unit can be provided in another form, such as, without limitation, a liquid, gel, or oil, as long as the liquid, oil, or gel does not detrimentally interfere with the dissolution properties of the separators. The amount of drug per dose unit will vary depending upon the drug or drugs to be delivered and the desired plasma profile. In one embodiment, the dose units are provided as deposits.

A deposit is made by a method that suitably applies a controlled amount of a drug onto a substrate. One method for doing this is electrostatic deposition of a dosage amount of the drug onto an appropriate substrate. Key elements of electrostatic deposition technology include (1) the attachment of a film substrate to a patterned receiving module; and (2) the controlled deposition of pure pharmaceutical powder onto the substrate film. Electrostatic deposition techniques are described, for example, in U.S. Pat. Nos. 5,753,302, 5,788,814, 5,858,099, 5,846,595 to Sun et al., U.S. Pat. No. 5,871,010 to Datta et al., U.S. Pat. No. 5,669,973 and U.S. Pat. No. 5,714,007 to Pletcher et al., and PCT/US99/12772 by Chen et al, filed on Jun. 8, 1999. All these patents and patent applications are incorporated by reference herein.

In general, for making a deposit by electrostatic deposition, the drug powder is charged and transported to a chamber where dispersion and deposition take place. Deposition is achieved by establishing a pattern of charges of one polarity on a substrate where deposition is desired, and delivering a supply of the material to be deposited, in the form of small, oppositely charged, particles. The attractive Coulomb force created within the system accelerates and focuses the particles toward the desired regions of the substrate.

In one embodiment, the drug powder is supplied by a powder feed mechanism to a charging module where a static surface charge is placed on small particles of the drug powder. The charged drug powder is then transported using precisely controlled gas flow to a chamber in which it is dispersed as a cloud. The powder is uniformly dispersed in the chamber by a combination of electrostatic forces and aerodynamic design.

Above the chamber, a pattern of opposite charges is established by an electrostatic receiver onto a substrate (e.g., a polymer film). The charged drug powder is attracted to the substrate and deposited in a pattern of small dots. By accurately controlling the electric field, the system deposits precise amounts of drug powder in many locations on the substrate simultaneously.

The deposition substrate is preferably an insulating film. In one embodiment, charging is performed using a three-layer structure that has a conducting backplane electrode, an insulating layer, and a patterned conducting top electrode. This patterned top electrode is segmented into shielding electrodes that are areas electrically connected to ground and floating electrodes that are electrically isolated from the shielding and backplane electrodes. Application of a positive voltage to the backplane electrode establishes a positive surface charge in the backplane electrode. Charges that mirror the backplane charges are induced in the conductive top electrodes. In the shielding electrodes, the negative mirror charges are supplied from the ground connection and totally compensate the charges in the backplane electrode so there is no external electric field established. In the floating electrodes, the negative mirror charges induced by the charges in the backplane electrode are supplied by charge separation within the floating electrode. The negative charges compensate the charges in the backplane electrode, leaving uncompensated positive charges on the top surface of the floating electrode. These induced positive charges in the floating electrode produce an electric field that is used to control the electrostatic deposition process.

Confirmation of the drug content of each deposit can be accomplished using a laser-based technique similar to barcode reading. This enables the on-line, non-destructive testing of each dose. This compares favorably to conventional pharmaceutical products where inspection relies on off-line quality inspection of small samples, and products pass inspection based on statistical principles.

In some embodiments, the dose unit is sealed in place on the deposition substrate by attaching a cover to the deposit. In one embodiment, the cover is attached by bonding it to the substrate. The cover is bonded to the substrate around the perimeter of the deposited drug. The sealing process entraps the powder between the substrate and cover layers, forming a laminate. The areas of deposition are then "punched out" or otherwise formed into discrete deposits.

As will be appreciated by those skilled in the art, bonding or lamination can be achieved using a variety of methods, including, without limitation, ultrasonic techniques, thermal techniques such as laser or heat sealing, or via chemical means such as solvent evaporation or adhesive. A suitable ultrasonic welding head is the 900 M-Series™ ultrasonic welder available from Branson Ultrasonics Corporation in Danbury, Conn.

Methods and equipment for achieving the foregoing electrostatic deposition are described in the above referenced patents and patent application. These and other known methods and apparatuses for deposition and formation of laminates can suitably be used.

Material suitable for use as a substrate for electrostatic deposition possesses the following general characteristics: consistent electrical properties; adequate mechanical stability; optical properties suitable for dose measurement. In some embodiments, substrate-suitable materials exhibit one or more of the following additional characteristics: is suitable for lamination, possesses pharmaceutical acceptability; and is non-reactive with the drug powder(s). Illustrative materials suitable for use as a substrate for an electrostatic deposition process include, without limtation, polymers, nonwoven fabrics, paper, inorganic materials such as metal salts and metal alloys, and cellulose materials.

The deposition substrate advantageously comprises a polymeric substance that dissolves in body fluids. In an alternative embodiment, the substrate is an indestructible substance that is readily eliminated from the body once the drug has been released from the dose unit into the body. Polymers suitable for use as a deposition substrate include, without limitation, polyvinylacetate, polyvinylakahol, polyvinylpyrrolidone (PVP), polyethylene oxide (PEO), gelatin, modified starches, and celluloses such as hydroxypropylmethyl cellulose (HPMC), methyl cellulose (MC), ethyl cellulose (EC), and hydroxypropyl cellulose (HPC).

The polymeric substance for use as a deposition substrate is advantageously available as a film. In some embodiments, the film includes a plasticizer to increase the flexibility of the film. A suitable plasticizer is polyethylene glycol (PEG); other plasticizers suitable for use are known to those skilled in the art.

The substrate can have any thickness so long as it functions as described above. In general, the thickness will be between about 0.0002 and 0.2 inches, desirably about 0.001 inches (0.0254 mm).

Release of the drug from the substrate can be immediate, upon exposure to an environment in which the substrate or the drug is soluble, such as gastric fluid. Alternatively, drug release can be dependent, to varying degrees, upon dissolution of the substrate in the environment. Accordingly, in some embodiments, the deposition substrate is a factor in the overall release profile of the dosage form, while in other embodiments, it has an insignificant effect.

As described above, a deposit cover can be used if desired to form a laminate comprising the substrate, the dose unit, and the cover. Use of a cover is not necessary but can be advantageous to provide structural integrity to the deposits. The cover need not have the same electrical properties as the substrate, but should exhibit adequate mechanical stability; properties suitable for lamination; pharmaceutical acceptability; and non-reactivity with the drug powder(s).

Like the deposition substrate, in some embodiments, the deposit cover is a factor in the overall release profile of the dosage form, while in other embodiments, it has an insignificant effect. To that end, in some embodiments, a cover film can be used that provides modified release of the drug. Delayed release of the drug can be provided by use of a cover that has delayed dissolution in the environment. Continuous release can be provided through use of a cover that allows controlled transport of the drug through the cover. For example, the cover can be made of a material that forms a gel upon contact with gastric fluid. Alternatively, the deposit cover film can be made of a material that dissolves very quickly, this providing immediate exposure of the dose unit to a particular environment, such as gastric fluid.

In some embodiments, the deposit cover comprise a polymeric film such as, without limitation, polyvinylacetate, polyvinylalcohol, polyvinylpyrrolidone (PVP), polyethylene oxide (PEO), gelatin, modified starches, and celluloses such as hydroxypropylmethyl cellulose (HPMC), methyl cellulose (MC), ethyl cellulose (EC), and hydroxypropyl cellulose (HFC). It is within the capabilities of those skilled in the art to select a material to provide the desired release characteristic. The cover can be the same material as the substrate or it can be a different material.

The deposit cover can have any thickness so long as it functions as described above. In general, the thickness will be between about 0.0002 and 0.2 inches, desirably about 0.001 inches (0.0254 mm), consistent with substrate thickness.

The dosage form includes one or more separators to control the exposure of dose units to the environment, such as gastric fluid. In the illustrative embodiments, one separator is used to control exposure of each dose unit; however, in other embodiments, more than one separator may be used for each dose unit or more than one dose unit may be controlled by a single separator.

A key criterion for the design of a dosage form and selection of the separators to use is the desired rate of dissolution of the separators. Variables that affect the dissolution rate include the material used, the thickness of the material, and the design of the dosage form such as, for example, the area of separator exposed to the environment. Usually, the separators provide for a decrease in the release rate of the drug from a dose unit, as compared to immediate release of the drug from the same type of dose unit In particular, in some embodiments, the decrease in release rate is such that a dosage frequency of less than about 50% of a comparable immediate release dosage form is required to maintain generally the same drug plasma level.

The separators are advantageously made of a material that has adequate mechanical stability; pharmaceutical acceptability; and non-reactivity with the drug powder(s). Complete dissolution of each separator is desirable in order for the dissolution from inner layers of the dosage form to be independent of the outer layers. Many different types of materials can be used for the separators, such as polymers in the form of films and plugs, and matrix type materials such as inorganic materials. In some embodiments, nonwoven fabrics are used. Polymers suitable for use as a separator include, without limitation, polyvinylacetate, polyvinylalcohol, polyvinylpyrrolidone (PVP), polyethylene oxide (PEO), gelatin, modified starches, and celluloses such as hydroxypropylmethyl cellulose (HPMC), methyl cellulose (MC), ethyl cellulose (EC), and hydroxypropyl cellulose (MFC).

In some embodiments, materials that swell slightly upon wetting are used because expansion improves seal integrity. The separators can have any thickness so long as they function as described above. In general, the thickness will be between about between about 0.001 and 0.2 inches. In a preferred embodiment, the separators are polymeric films having a thickness of about 0.007 inches (0.178 mm).

The separators provided in a single dosage form can be the same or different. For a particular drug or drug combination it may be desirable, for example, to deliver a dose unit at alternating two and four hour intervals. A dosage form can be designed to deliver two or more different drugs, at different time intervals, thereby requiring the use of separators having different rates of dissolution. The separators may differ, for example, in the type of material or in their thickness in order to achieve desired differences in overall dissolution rates.

The dose units are assembled into controlled release multi-step dosage forms that can have a variety of designs. Controlled release is achieved primarily through the selection of separators having desired dissolution rates. Secondary control parameters include the selection of substrates and covers, as discussed above, and other dosage form structural elements having various dissolution and/or drug release characteristics. The particular release profile desired for a particular drug can be achieved using structural elements having appropriate dissolution and/or release characteristics for that drug to achieve the desired profile.

One advantage of dosage forms in accordance with the illustrative embodiment of the present invention is the ability to perform testing on each individual element to determine its effect on the overall dosage form and the dosage form release profile. For example, compatibility testing can be performed on each element to ensure that it does not affect the stability or activity of the drug or drugs, as well as the other elements. In addition, independent dissolution testing can be performed on each element or combination thereof, and on variations of each element, to determine the appropriate design for that element.

With reference to FIG. 1, a first dosage form 10 in accordance with the illustrative embodiment of the present invention is a capsule. Dosage form 10 includes side-wall 12, first end 14, second end 16, five dose units 18 and five separators 20, interrelated as shown.

Side-wall 12 and second end 16 are impermeable, and first end 14 is either open or capped by a rapidly soluble material. Each of the five dose units 18 are protected from exposure to an ambient environment (e.g., gastric fluid, etc.), by separators 20. Each separator 20 is a plug or membrane that abuts, and seals to, the inside of side-wall 12.

As gastric fluid, etc., dissolves separator 20 proximal to first end 14, the first dose unit 18 is exposed. As soon as the gastric fluid, etc., dissolves the substrate and cover materials of exposed dose unit 18, the drug contained therein is released. The gastric fluid sequentially dissolves the remaining separators 20, with the concomitant release of drug as each successive dosage form 18 is exposed.

In a basic or simple embodiment, the substrate and cover materials of dose units 18 dissolve very quickly upon exposure to the gastric fluid, etc., so that the drug contained therein is released very quickly upon such exposure. In such an embodiment, separators 20 substantially control the release of the drug from dosage form 18. It will be understood that in other embodiments, fewer than or more than the five dosage forms 18 and the five separators 20, as depicted in FIG. 1, may suitably as used.

Figure 2:
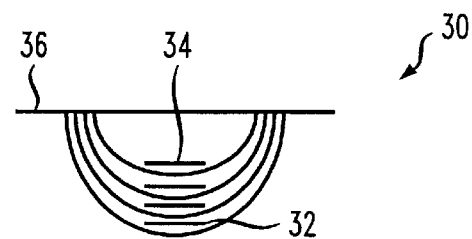
FIG. 2 depicts a second dosage form in accordance with the illustrative embodiment of the present invention.

FIG. 2 depicts a second dosage form 30 in accordance with the illustrative embodiment of the present invention. Dosage form 30 includes nested separators 32. In the embodiment depicted in FIG. 2, separators 32 are hemispherical in shape and have a flat flange-like region depending from the edge thereof. The flange-like region of each of the separators 32 are sealed together at base region 36. A flat impermeable film covers base region 36 and seals the open portion of inner-most separator 32. Adjacent separators 32 enclose a single dose unit 34 of drug. Drug can be deposited directly onto the separators 32, or can be in form of discrete deposit.

Separators 32 are configured so that they dissolve successively. In embodiments in which dose units 34 dissolve rapidly, the release profile is controlled by the time required to dissolve each separator 32.

For oral administration, the dosage forms (e.g., dosage forms 10 and 30, etc.) are advantageously designed for release of drug from a dose unit at a frequency ranging from release once about every hour to release once about every 12 hours. Preferably, release of drug occurs once about every 2 hours to once about every 6 hours. Since the maximum time that a typical oral dosage form will remain in the body is about 24 hours, the dosage forms of the invention will contain from about 2 to 24 dose units, preferably about 4 to 12 dose units. Of course, these numbers will vary for dosage forms for other routes of administration and for oral dosage forms that can be retained for longer than about 24 hours.

In one embodiment, the dosage form can have a delayed release aspect wherein a separator is used to prolong the rate of exposure of the first dose unit until several hours past ingestion, so that administration of drug does not begin until the early morning, for example. This can be useful for administration of drugs for indications that are more prevalent in the morning such as asthma and heart attacks, for example. This effect can also be achieved using an overwrapping or capsule cover that does not make the dosage form available until a certain length of time after administration.

In another embodiment, the dosage form is designed to release drug for an initial period of time, followed by a period of time in which drug is not released. In this case, the dosage form is made with a thicker or more slowly dissolving separator designed to initiate the beginning of the non-release period.

The dose units and separators are preferably encased in a structural form to provide integrity to the dosage form. The dose units and separators can be assembled into a capsule or tablet form, for example, and covered with one or more overwrappings. In some embodiments, such as the embodiment depicted in FIG. 1, the dosage form includes a wall or housing made of a water-impermeable material, to protect the dose units and separators from unwanted dissolution. A commonly used water-impermeable material that can be employed is wax, such as a combination of paraffin and microcrystalline wax. Other commonly used materials include carnauba wax and beeswax. Those of skill in the art will be familiar with other materials that are suitable for use. As desired, an overwrapping can be used to protect the dosage form until it reaches the intended site of administration, such as the stomach cavity, or to delay drug release until a certain amount of time after administration. For release in the stomach, the overwrapping is advantageously acid-soluble. Suitable acid soluble materials include, without limitation, polyvinyl pyrrolidone and amine substituted acrylic copolymers. For release in the small intestine, the overwrapping is advantageously alkaline soluble and/or enzyme biodegradable. Suitable alkaline soluble materials include carboxyl substituted acrylic copolymers and polymeric derivatives of alginic acids. Overwrappings are also useful for protecting the dosage form, during shipping and handling.

One or both ends of the dosage form are left "open," that is, not covered with the impermeable material. The ends can be uncovered, or can be covered with another material that rapidly dissolves or is permeable.

In one embodiment, spacers are used to provide structural support for the dose units and the separators. The spacers are advantageously configured as annular rings, having an interior void sufficient to hold a dose unit therein. The spacers are preferably made of a material that dissolves faster than the dose units so that they do not affect dissolution of the dose units and do not contribute to the release profile. The spacers can be made of any relatively quickly dissolving material that does not interfere with the drug or the other materials. Appropriate materials include polymers, nonwoven fabrics, inorganic materials such as metal salts and metal alloys, and cellulose materials. Polymers that can be used include, but are not limited to, polyvinylacetate, polyvinylalcohol, polyvinylpyrrolidone (FVP), polyethylene oxide (PEO), gelatin, modified starches, and celluloses such as hydroxypropylmethyl cellulose (HPMC) and methyl cellulose (MC), and hydroxypropyl cellulose (HPC). Low molecular weight HPMC is one preferred material. An appropriate thickness for the spacers is generally from about 0.005 to 0.2 inches, more desirably about 0.01 to 0.06 inches.

In some embodiments, the dosage unit is assembled by layering the spacers, dose units, and separators and then applying the overwrapping to the assemblage. In one embodiment, the spacers, dose units, and separators can be deposited directly into the overwrapping, such as when the overwrapping is a capsule shell. The dose units can be independently manufactured and then assembled into the dosage forms along with separators and, optionally, other elements such as spacers and overwrappings. Alternatively, drug can be directly deposited onto a separator or a substrate or can be otherwise directly deposited into the interior void of a spacer. Any standard method of accurately metering powder can be used to deposit a dose amount of powdered drug into the interior void of a spacer. Those skilled in the art will conceive of many ways in which the dosage forms of the invention can be manufactured.

A dosage form in accordance with the illustrative embodiment of the present invention is about the size of standard dosage forms. Because substantially pure drug can be used in deposits, the dosage form can be substantially smaller than presently used dosage forms. The diameter of the dosage forms would desirably not be more than about 0.5 inches.

Many active agents can be formulated into the dosage forms. The dosage forms are particularly suited to delivery, from the same dosage form, of multiple drugs that require different release profiles. Examples of drugs that can be formulated into the dosage forms include synthetic and isolated organic and inorganic compounds or molecules, proteins and peptides, polysaccharides and other sugars, lipids, and nucleic acid molecules. The active agents can have any of a variety of activities or functions, which may be inhibitory or stimulatory, including, without limitation, materials that act upon the central nervous system such as hypnotics, sedatives, psychic energizers, tranquilizers, antidepressants, and anticonvulsants; muscle relaxants; muscle contractants; antiparkinson agents; agents having antibiotic activity, antiviral activity, antifungal activity, steroidal activity, cytotoxic or anti-proliferative activity, anti-inflammatory activity, analgesic or anesthetic activity, anti-HIV agents, antiemetics, pain relievers, hormones, antiangiogenic agents, antibodies, neurotransmifters, psychoactive drugs, drugs affecting reproductive organs, and oligonucleotides such as antisense oligonucleotides, as well as contrast or other diagnostic agents. A description of these classes of drugs and listing of species within each class can be found in Martindale, The Extra Pharmacopoeia, 31st Ed., The Pharmaceutical Press, London (1996) and Goodman and Gilman, The Pharmacological Basis of Therapeutics, (9th Ed., McGraw-Hill Publishing Company (1996).

The amount of drug that will be incorporated in a dose unit varies widely depending on the particular drug, the desired therapeutic effect, and the time span necessary for the drug to be released. Since a variety of dose units in a variety of sizes, shapes and compositions are intended to provide complete dosage regimes for therapy for a variety of maladies, there is no critical upper limit on the amount of drug incorporated in the dose units of the invention. The lower limit, too, will depend on the activity of the drug and the time span of its release from the units. Thus, it is not practical to define a range for the therapeutically effective amount of drug to be released by the individual units or by the dosage form as a whole.

The dose units advantageously provide a variety of drug delivery profiles depending upon their composition. They can all contain the same drug or drugs at the same concentration(s) to deliver identical pulses of drug over time as drug is released from each dose unit, or they can contain the same drug(s) at different concentrations to give different pulses of drug. The dose units in a single dosage form can contain different drugs and provide any manner of pulsed release of those drugs, including superimposed delivery, if desired.

In one embodiment, the dosage form also includes an immediate release component so that an initial drug level is achieved. The immediate release portion can be provided as one or more deposits or can be provided in a conventional form, such as a compressed matrix. The immediate release component can be affixed to the extended release component or can be encapsulated in one or more overwrappings with the extended release component. Upon dissolution of the overwrapping(s), the immediate release portion will become available for dissolution.

Figure 3:
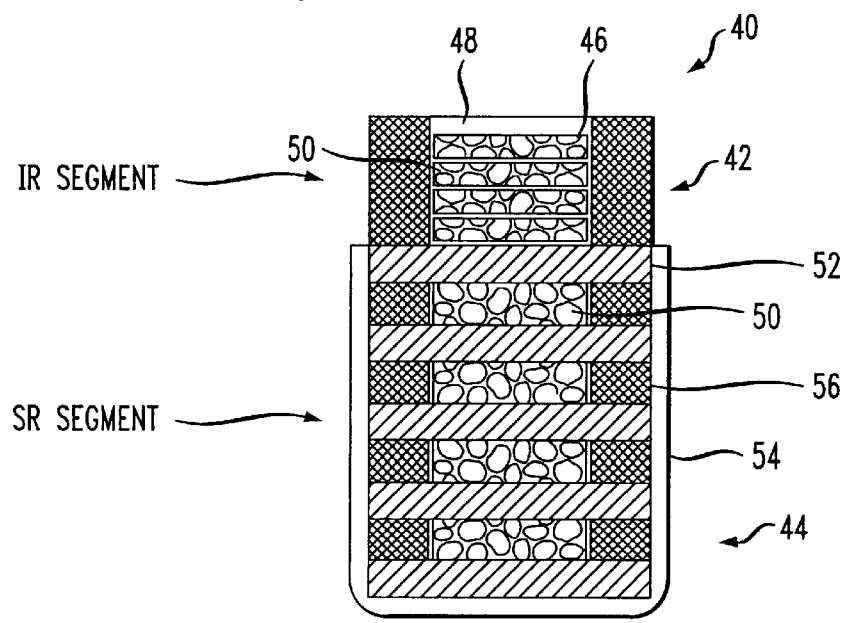
FIG. 3 depicts a controlled release system having an immediate release component and an extended release component in accordance with the illustrative embodiment of the present invention.

FIG. 3 depicts dosage form 40 that includes an immediate release section 42 and an extended release section 44. The immediate release section 42 includes four deposits 50 that are not separated by separators. In a first alternative embodiments immediate release section 42 is formed with a single deposit. In a second alternative embodiment, immediate release section 42 comprises a conventional immediate release formulation.

Immediate release section 42 has a dissolvable barrier 48 on the end thereof. In various embodiments, barrier 48 dissolves: (1) immediately; (2) in a desired amount of time after ingestion; and (3) upon reaching the desired administration site, such as the gastric cavity.

Extended release section 44 includes four deposits 50 that are separated from immediate release section 42, and from each other, by separators 52. The outside of dosage form 40, except for immediate release section 42, is encased in an impermeable housing 54. Spacer rings 56 provide support for deposits 50.

It is to be understood that the number of deposits 50 in immediate release section 42 need not be equal to the number of deposits 50 in extended release section 44. Furthermore, immediate release section 42 and extended release section 44 can contain fewer or more than the four deposits 50 depicted in FIG. 3.

In the absence of excipients, the physical appearance of the dosage forms may be very different from a traditional tablet. To that end, in some embodiments inactive excipients are added to "bulk up" the dose units or the dosage forms to render them more like conventional capsules or tablets. In fact, the dose units can be quite small, such that in some cases it is advantageous to sandwich dose units between two larger films to increase their size to make them easier to handle for processing. Although the manufacturing process itself requires no excipients, if they are needed for functional reasons like bioavailability or dissolution they can be deposited after the drug onto the substrate or otherwise included in the dose unit. Other ingredients can also be added to the dosage forms, by deposition along with the drug, or by incorporation into one of the materials, such as the separator. For example, it might be advantageous to include an antioxidant in the dosage form, to protect drugs that oxidize easily.

Design of the dosage form will be controlled in major part by the desired plasma profile. The correlation between the desired in vivo plasma profile and an in vitro dissolution profile of the drug (in vitro, in vivo correlation (IVIVC)) can be used in design and testing of the dosage form. The in vitro dissolution profile of a dosage form made in accordance with the illustrative embodiment of the present invention can be measured by means known to those skilled in the art. The IVIVC is known for many drugs or can be determined by those skilled in the art according to generally recognized methods. Such methods are generally described, for example, in a publication published in September 1997 by Food and Drug Administration, Center for Drug Evaluation and Research, entitled "Guidance for Industry, Extended Release Oral Dosage Forms: Development, Evaluation, and Application of In Vitro/In Vivo Correlations". Computer software is commercially available for predicting plasma profiles from orally delivered drugs.

In many cases, the desired release profile includes an initial release of drug to achieve a base drug level, followed by extended release to substantially maintain the base level. The extended release is achieved by a plurality of pulse releases in the invention. Accordingly, several parameters that should be considered in design of the dosage form to achieve a desired release profile are:

the amount of drug needed in the immediate release component;

the time in which the immediate release should be achieved;

the amount of drug that needs to be released in each pulse;

the amount of time in which each pulse of drug should be released; and the total time of pulsed release.

Additional parameters to be considered in design of the dosage form to achieve a desired release profile are:

include the amount of drug per dose unit;

the number of dose units;

the material(s) used for the dose unit substrate and cover;

the material(s) used for separators;

whether one or both ends are exposed;

the material(s) used for any over-wrappings;

the thickness and number of polymeric layers used for the substrate, the cover, the separators, and the overwrappings; and the manner in which the dose units are assembled.

All of these parameters can be controlled in the dosage forms in accordance with the illustrative embodiment of the present invention.

The dosage forms achieve extended release because the individual dose units within a dosage form are dissolved successively. In some embodiments, the release profile comprises small pulses of medication over a prolonged time span. In some cases, it is preferable to design the dosage form to have overlapping drug release, so that "spikes" of drug release are avoided.

The dosage forms described herein are useful for controlled delivery of a variety of drugs. The dosage forms include an extended release portion and are particularly useful for delivery of a drug or drugs for an extended period of time. While the illustrative dosage forms are described in the context of oral dosage forms, the same designs can generally be used for other dosage forms such as vaginal and rectal suppositories. In the case of these other dosage forms, as well as implants, the separators are advantageously formed from more slowly dissolving materials, since the time of residence of the dosage form will be substantially longer than the about 24 hour residence time of oral dosage forms. Indeed, drug delivery from implants takes place over the course of weeks or months. To achieve such protracted erosion, biodegradable polymers are advantageously used. These are insoluble polymers that gradually break down in vivo. Example include, without limitation, polyorthoesters, lactide and glycolide polymers and copolymers, polyesteramides, and hydroxybutyrate-hydroxyvalerate co-polymers.

In some embodiments of dosage forms in accordance with the illustrative embodiment of the present invention, the dosage form includes a dissolution-enhancing amount of a surfactant. The surfactant is advantageously incorporated into/onto the separators (e.g., separator 20, separator 32, separator 52). In an alternative embodiment, the surfactant is incorporated into/onto the deposition substrate. In a further alternative embodiment, the surfactant is incorporated into/onto the deposit cover. In yet further embodiments, the surfactant is incorporated two or more of the above elements (e.g., into/onto the separator and deposition substrate, etc.).

As the surfactant-containing element (e.g., separator, etc.) dissolves, surfactant is released in the immediate vicinity of a drug that has likewise been released from one or more dose units. The surfactant improves the dissolution, and, as a consequence, the bioavailability of hydrophobic drugs. The use of surfactants to improve dissolution of hydrophobic drugs is disclosed in U.S. patent application No. 09/925,348, filed Aug. 9, 2001 and entitled "Improved Solid Pharmaceutical Dosage Formulation of Hydrophobic Drugs," incorporated by reference herein.

In further embodiments of dosage forms in accordance with the illustrative embodiment of the present invention, many other types of pharmaceutical additives (instead of or in addition to a surfactant) are advantageously incorporated into/onto the separators, and/or deposition substrate, and/or deposit cover. Such pharmaceutically acceptable additives include, without limitation, antioxidants, antimicrobial agents, complexing agents, acidity boosting agents, alkalinity boosting agents, buffering agents, carrier molecules, chelating compounds, preservatives and the like. The use of such additives is described in further detail in 09/925,348, referenced above.

The dosage forms are also be useful for drug development. At early stage clinical trials, different strength formulations are needed to perform dose studies. A traditional tablet would need ten different formulations for ten different doses. With dosage forms in accordance with the illustrative embodiment of the present invention, the formulation could be the same, with merely a different amount of active ingredient being deposited in each case. This could lead to a marked reduction in early development time.

The invention is further illustrated by the following examples, which are provided by way of illustration, not limitation, and are not to be construed in any way as imposing limitations upon the scope of the invention. On the contrary, it is to be clearly understood that resort may be had to various other embodiments, modifications, and equivalents thereof, which, after reading the description herein, may suggest themselves to those skilled in the art without departing from the spirit of the present invention.

EXAMPLES

Example 1

Dosage Forms Containing Drug A

Drug A, 1,2,3,9-tetrahydro-9-methyl-3-[(2-methyl-1H-imidazol-1-yl)methyl]-4H-carbazol-4-one, is used for prevention of nausea and vomiting associated with initial and repeat courses of emetogenic cancer chemotherapy, and for treatment of diseases of the central nervous system, migraines, and gastrointestinal disorders.

Compatibility studies were conducted to assess the compatibility of Drug A with several polymeric films, to determine an appropriate material for the substrate. The films studied were an HPMC film, an. HPMC/HPC blend film, and a polyvinyl alcohol film. Each film was cut into pieces approximately 0.5 cm square and a piece of each film was placed into a glass bottle. Approximately 500 mg of Drug A was added to each bottle. The bottles were closed with Teflon lined plastic caps. Bottles of Drug A and each of the films separately were prepared and used as controls.

The controls and drug/polymer samples were stored in a closed chamber under the following conditions, and tested at the indicated time periods:

A) 25° C.±2° C.; 60% RH±5%; tested at 2,4 and 12 weeks;
B) 40° C.±2° C.; 75% RH±5%; tested at 2,4 and 12 weeks;
C) 40° C.±2 $S^C$; 75% RH±5%, open bottle; tested at 2, 4 and 12 weeks; and
D) 50° C.±2*C.; no humidity control; tested at 2,4, and 8 weeks.

At each time point, the samples were tested for chromatographic purity. Each of the polymers was deemed acceptable because no changes in purity of Drug A were noted as compared to the control samples. Several dosage forms were made, as outlined in Table 1. "ER" refers to the extended release portion. "HPMC, HPC" refers to a hydroxypropyrmethyl cellulose, hydroxypropyl cellulose copolymer. "PEO" refers to a polyethylene oxide polymer, "HPMC, PEG" refers to hydroxypropylmethyl cellulose containing polyethylene glycol (PEG) plasticizer.

TABLE 1

Dosage Forms With Drug A

| Sample | ER portion (total mg) | ER design (layers * mg/layer * hours/layer) | Separators (0.001 inch) | FIG. |
|---|---|---|---|---|
| 1 | 24 | 6 * 4 * 3 | HPMC, HPC | 4 |
| 2 | 24 | 9 * 2.44 * 2 | HPMC, HPC | 5 |
| 3 | 24 | 4 * 6 * 4.5 | HPMC, HPC | 6 |
| 4 | 24 | 6 * 4 * 3 | PEO | 7 |
| 5 | 24 | 6 * 4 * 3 | HPMC, PEG | 8 |

The dosage forms were assembled manually, by stacking the separators and spacers. Powdered drug was deposited into the voids of the spacers. The assemblage was dipped into molten wax to form an overwrapper.

Dissolution testing of the assembled dosage forms was performed using a Distek Model 2100B dissolution bath configured as USF Apparatus II (paddles). The paddle rotation was set at 50 rpm. The dissolution medium was 900 ml of pH 6.8 phosphate buffer at 37° C. In two experiments, the dosage units were caged with copper wire prior to introduction to the dissolution vessel. This maintained the dosage unit in a fixed orientation at the bottom of the vessel. In one experiment the dosage units were not caged.

A Distek Model 2230 Dissolution sampler was used to automatically collect samples from each of the dissolution vessels. Samples were taken at 30 minutes, 1 hour, and 1½, 2,2-/2, 3, 4, 5, 6, 8, 10, 12, 14, 16, 18, 20, 22, 24, and 30 hours. Three samples of each formulation were tested. The collected samples were then analyzed by reversed phase HPLC using a Waters Spherisorb S5 CN-RP column, 4.6× 150 mm. The mobile phase was a filtered and degassed mixture of 0.02 M monobasic potassium phosphate (pH 5.4) and acetonitrile (50:50), The 0.002 M potassium phosphate was prepared by dissolving 2.72 g of monobasic potassium phosphate ($KH_2PO_4$) in water and diluting to 1000 ml with water. The pH was adjusted to 5.4 with 1 M sodium hydroxide. The injection volume was 20 micro-liters, a flow rate of 2,0 ml/min was used, and detection was at 216 nm.

Figure 4:
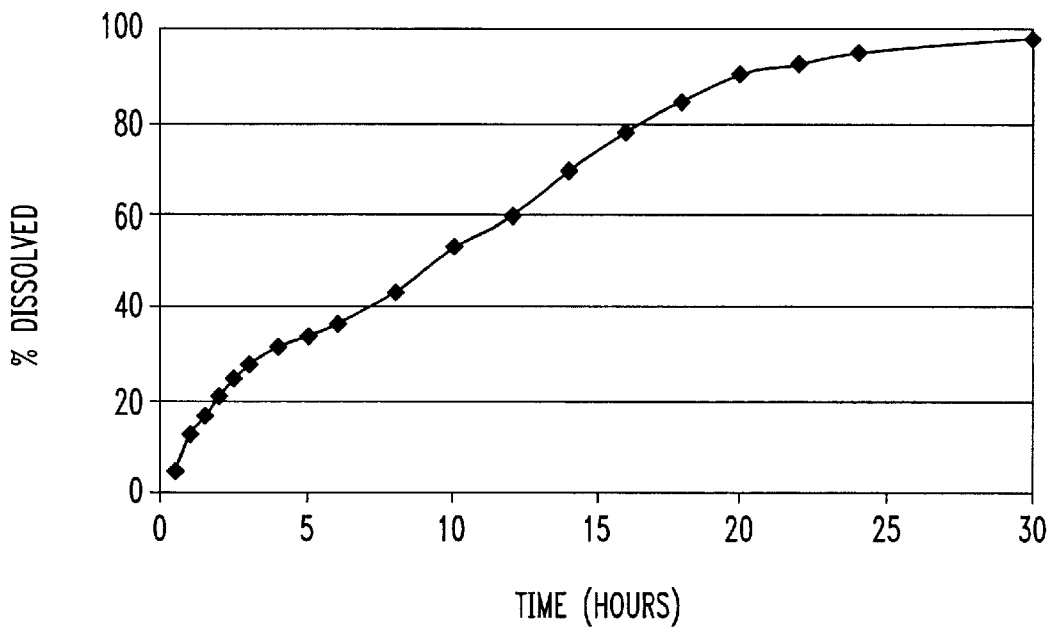
FIG. 4 depicts a dissolution profile for a dosage form in accordance with the illustrative embodiment of the present invention supplying Drug A, having a six-layer extended release section providing 4 mg pulses every 3 hours thereafter. The separators are formed from an HPMC, HPC film.
Figure 5:
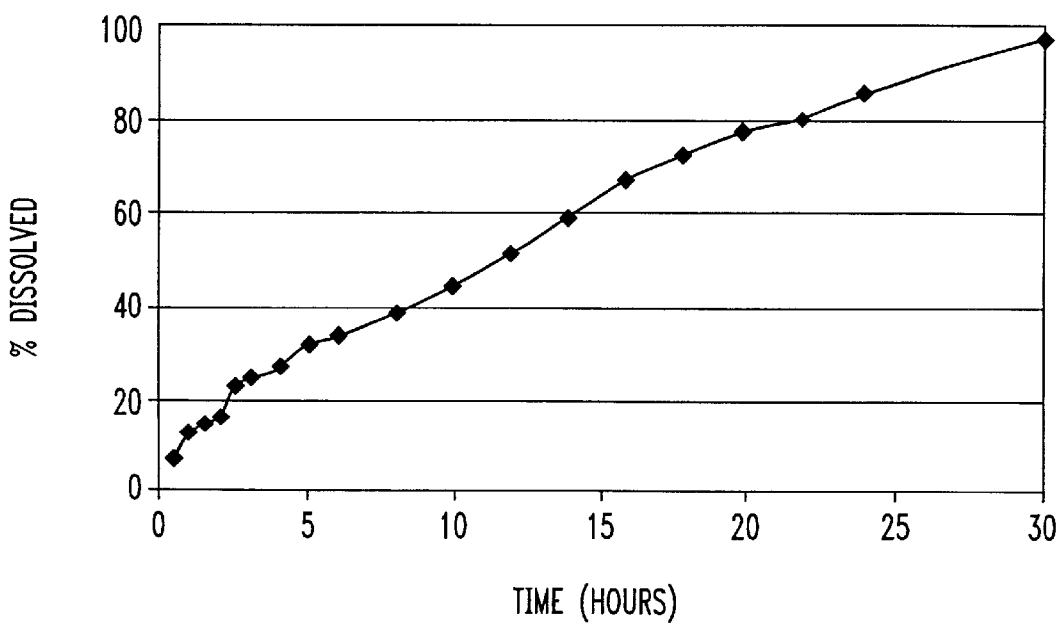
FIG. 5 depicts a dissolution profile for a dosage form in accordance with the illustrative embodiment of the present invention supplying Drug A, having a nine-layer extended release section, providing 2.44 mg pulses every 2 hours. The separators are formed from an HPMC, HPC film.
Figure 6:
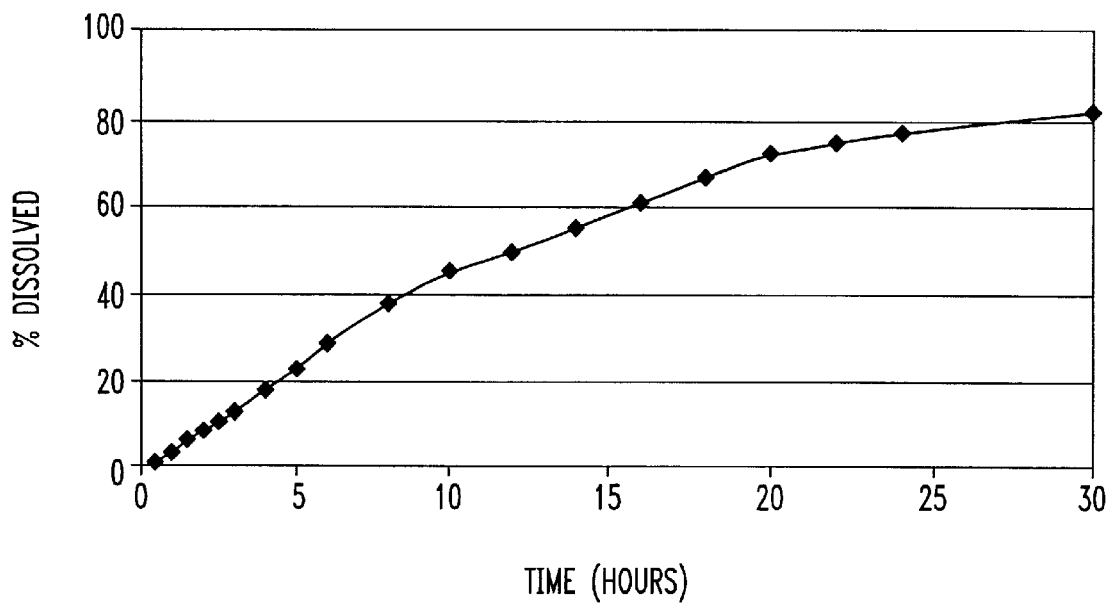
FIG. 6 depicts a dissolution profile for a dosage form in accordance with the illustrative embodiment of the present invention supplying Drug A, having a four-layer extended release component with deposits containing 6 mg each. The separators are formed from an HPMC, HPC film.

FIG. 4 depicts the results of dissolution testing for a dosage form having a 6-layer extended release component, designed to release 4 mg Drug A at 3 hour intervals. FIG. 5 depicts the results of dissolution testing for the dosage form having a 9-layer extended release component, designed to release 2.44 mg at 2 hour intervals. FIG. 6 illustrates the results of dissolution testing for a dosage form having a 6-layer extended release component with deposits containing 4 mg each, designed to release a dose unit at 4.5 hour intervals.

Extended release was seen, with the 6 layer system achieving nearly complete dissolution at approximately 24 hours, while the 9 layer system achieved nearly complete dissolution at approximately 30 hours. This experiment effectively demonstrates controlled release, and verifies that the number of layers is a significant variable with respect to the release profile. The dosage forms exhibited longer dissolution times than desired. This could be improved by using faster dissolving separators.

Figure 7:
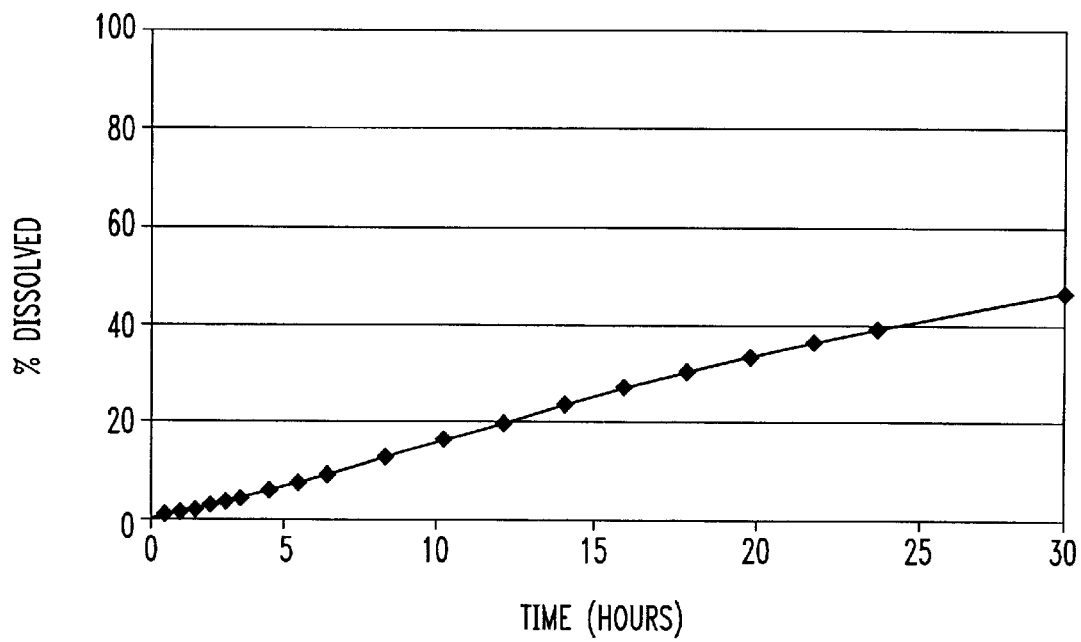
FIG. 7 depicts a dissolution profile for a dosage form in accordance with the illustrative embodiment of the present invention supplying Drug A, having a six-layer extended release section providing 4 mg 30 pulses every 3 hours thereafter. The separators are formed from a PEO film.

FIG. 7 depicts the dissolution profile of a dosage form having a 4-layer extended release component, with deposits containing 6 mg each, designed to release a dose unit at 3 hour intervals, where the separators were made with polyethylene oxide. PEO provides a more gradual release than the HPMC, HPC separator film (compare to FIG. 4). This demonstrates that the formulation of the separator film strongly affects the release profile. While this film led to a dissolution profile that is longer than is desired, the dissolution rate can be accelerated by using faster dissolving separators.

Figure 8:
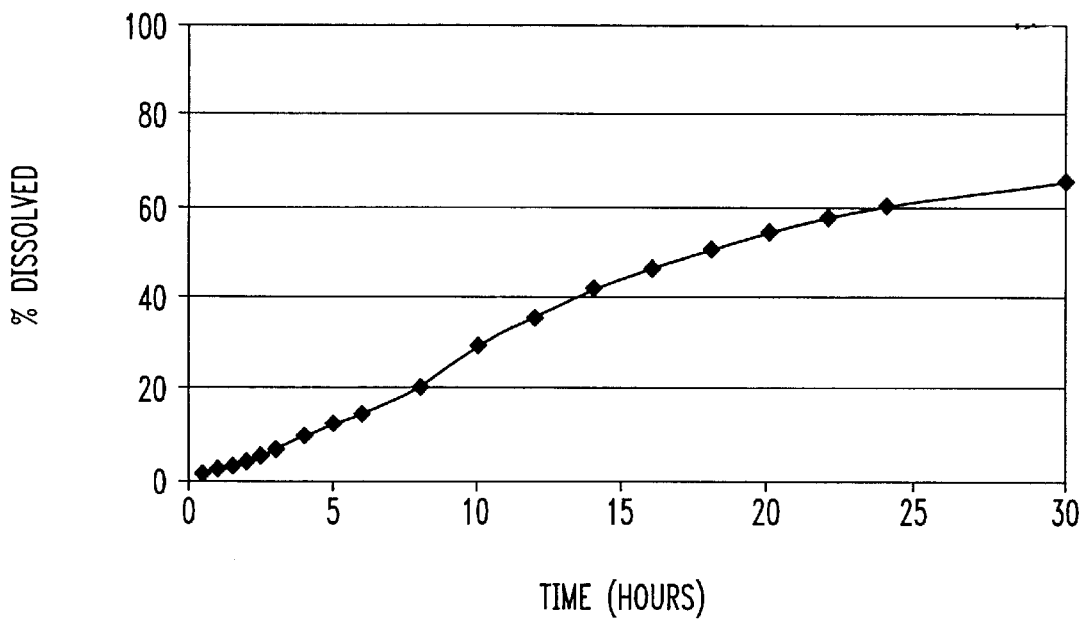
FIG. 8 depicts a dissolution profile for a dosage form in accordance with the illustrative embodiment of the present invention supplying Drug A, having a six-layer extended release section providing 4 mg pulses every 3 hours thereafter. The separators are formed from an HPMC/PEG plasticized film.

FIG. 8 depicts the results of dissolution testing of a dosage form having a 6-layer extended release component, designed to release 4 mg Drug A at 3 hour intervals, using an HPMC containing polyethylene glycol (PEG) plasticized film for the separators. The HPMC/PEG film provides a more gradual release than the separator film made of HPMC,HPC (compare to FIG. 4). This demonstrated that the formulation of the separator film strongly affects the release profile. While this film led to a dissolution profile that is longer than is desired, the dissolution rate could be accelerated by using a thinner film for the separators.

Example 2

Dosage Forms with Theophylline

Drug B, theophylline, is mainly used as a bronchodilator, and is a commonly prescribed agent for treatment of acute and chronic symptoms in asthma and chronic obstructive lung disease. This drug is a model compound that is currently available in several marketed controlled release products, and was selected because there is a good deal of literature regarding its pharnacokinetic/pharmacodynamic characteristics.

Three dosage forms were made using Drug B as the active compound. 10 mg deposits were used in a 5-layer dosage form and a 10-layer dosage form. In addition, a 5-layer dosage form having both ends open was made. The total dose of the 5-layer systems was thus 50 mg, and the total dose of the 10-layer system was 100 mg.

The dose units were made manually from a substrate and cover. The substrate film was formed into a dimple shape to provide a cavity for the drug and drug powder was weighed into the polymer film. Spacer rings were used to provide room for the dose unit, and to adhere dose units into a stack shape. The separator film was modified starch with water-soluble plasticizers.

Dissolution testing of the assembled dosage forms was performed using a Distek Model 2100B dissolution bath configured as USP Apparatus II (paddles). The paddle rotation was set at 50 rpm. The dissolution medium was 900 ml of simulated gastric fluid, pH 1.2, without enzymes and simulated intestinal fluid, pH 7.5, without enzymes maintained at a temperature of 37° C. The simulated gastric fluid and the simulated intestinal fluid were prepared according to USP23.

A Distek Model 2230 Dissolution sampler was used to automatically collect samples from each of the dissolution vessels. The volume sampled was 2.0 ml. Samples were acquired at the following times: 1 hour from the simulated gastric fluid and 3, 5, 7, 10, 12, 14, 16 and 20 hours from the simulated intestinal fluid. After one hour in simulated gastric fluid, the samples were removed and placed in dissolution vessels containing simulated intestinal fluid and testing was resumed (the 3 hour sample was acquired after 2 hours in the simulated intestinal fluid, the 5 hour sample after 4 hours, etc.)

The collected samples were analyzed by reversed phase HPLC using a Waters Spherisorb ODS2 column, 3.9×300 mm. The mobile phase was a filtered and degassed mixture of sodium acetate buffer and acetonitrile (70:30). The sodium acetate buffer was prepared by dissolving 2.72 g of sodium acetate trihydrate into a 2000-ml volumetric flask and adding approximately 200 ml of water. The mixture was shaken until the sodium acetate dissolves. 10.0 ml of glacial acetic acid was added and diluted to volume with water. The injection volume was. 10 $\mu$l, a flow rate of 1.0 ml/minute was used, and detection was at 271 nanometers.

Figure 9:
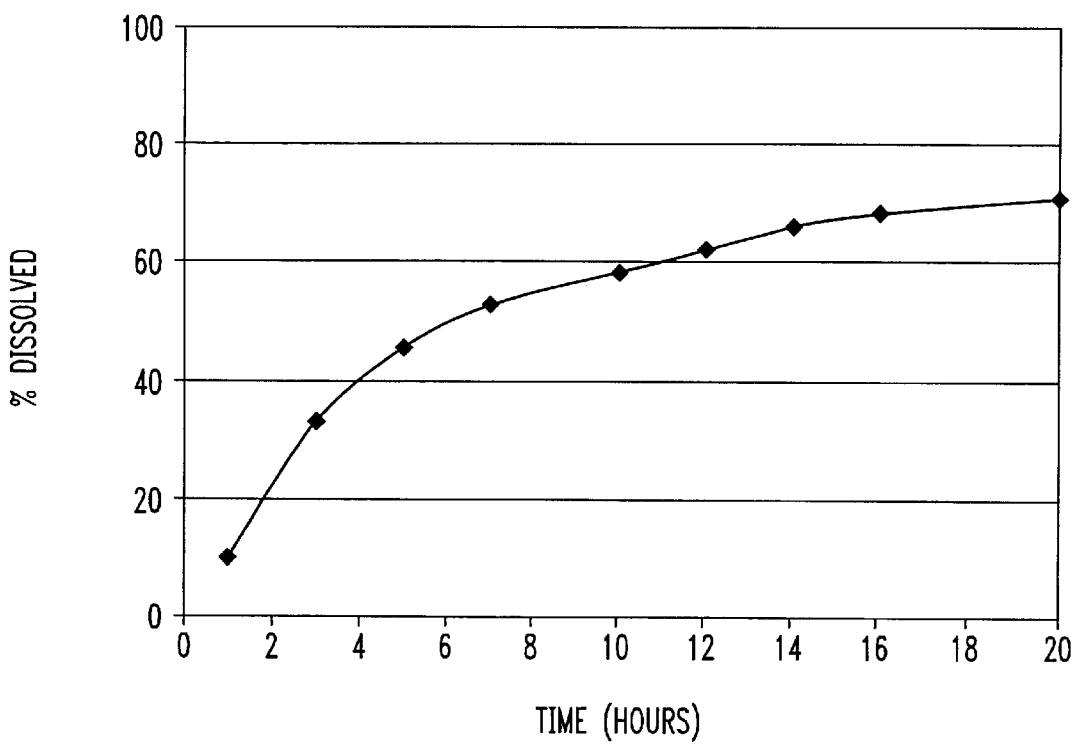
FIG. 9 depicts a dissolution profile for a ten-layer system in accordance with the illustrative embodiment of the present invention supplying Drug B.
Figure 10:
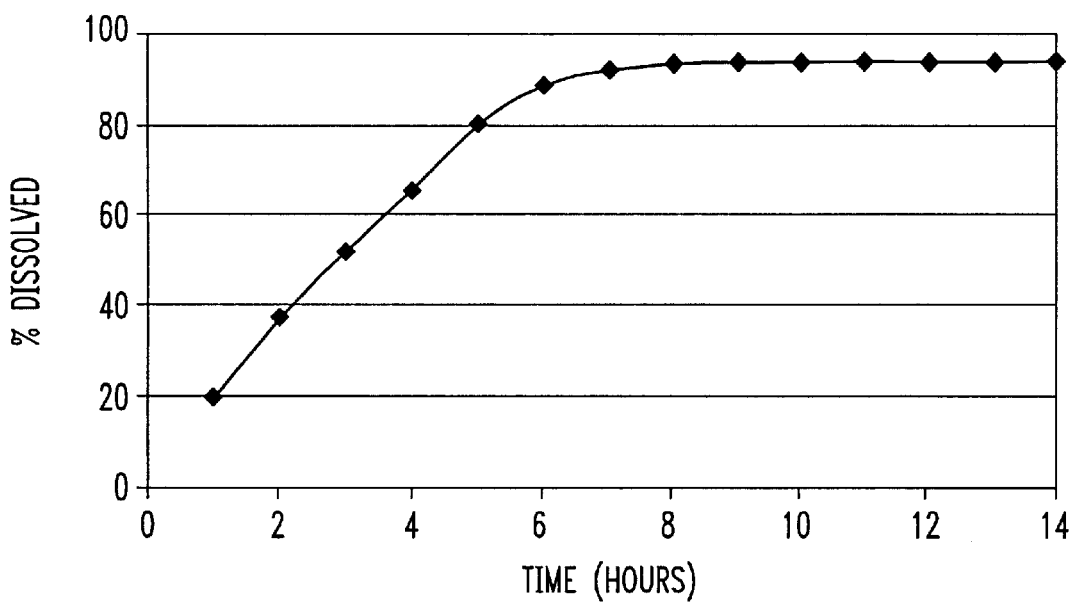
FIG. 10 depicts a dissolution profile for a five-layer system in accordance with the illustrative embodiment of the present invention supplying Drug B, with only one end exposed.
Figure 11:
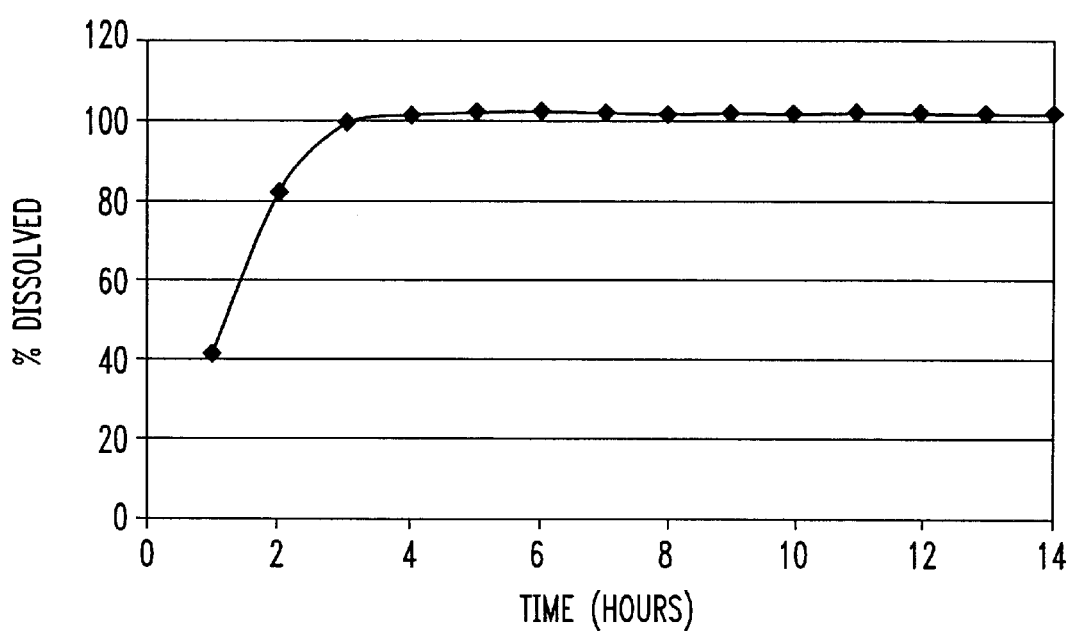
FIG. 11 depicts a dissolution profile for a five-layer system in accordance with the illustrative embodiment of the present invention supplying Drug B, with both ends exposed.

The results of dissolution testing for the 10-layer dosage form are depicted in FIG. 9. The 10-layer system gave approximately 70% release within 20 hours. FIG. 10 depicts the results of dissolution testing for the 5-layer dosage form having a housing comprising, at one end, impermeable wax. This 5-layer system gave nearly complete dissolution at 8 hours. The results of dissolution testing for the 5-layer dosage form that did not include impermeable material at either end are depicted in FIG. 11. As depicted in FIG. 11, complete dissolution was achieved in 3 hours. This work clearly indicates that the number of layers and the number of ends available for dissolution has a profound effect on dissolution.

Example 3

Animal Study

An in vivo study was conducted with Drug A using pigs as an animal model. The animal study evaluates the absorption profile of Drug A from a controlled release dosage form in accordance with the illustrative embodiment of the present invention as compared to an immediate release formulation (solution). The controlled release dosage form was designed to provide an apparent constant absorption of Drug A such that the plasma concentration over time would be relatively constant. The controlled release dosage form comprised 6-layers, each having 4 mg. of Drug A for a total of 24 mg. The separators comprised HPMC, 0.007 inches thick. Both the immediate release formulation (24 mg, Q8h×3) and the controlled release dosage form were administered intraduodenally.

Six pigs were surgically prepared with two vascular catheters and a duodenal cannula. One catheter was implanted into the right jugular vein, the second into the leftjugular vein. Both the immediate release formulation and the controlled release dosage form were administered via cannula directly into the duodenum. Pigs were fed ad libitum until being starved overnight (16–20 hours) prior to surgery. On the dosing day, the morning feed was withheld from the pigs and they received three-quarters of the total daily ration approximately four hours after dosing the controlled release dosage form or four hours after the first dose of the solution (i.e., the immediate release formulation).

Plasma samples were analyzed by LC/MS-MS. The dosage forms were recovered upon elimination from the animals to provide transit time estimates as well as estimates of the extent of drug release. A stability study was conducted with the dosage forms, as well.

Figure 12:
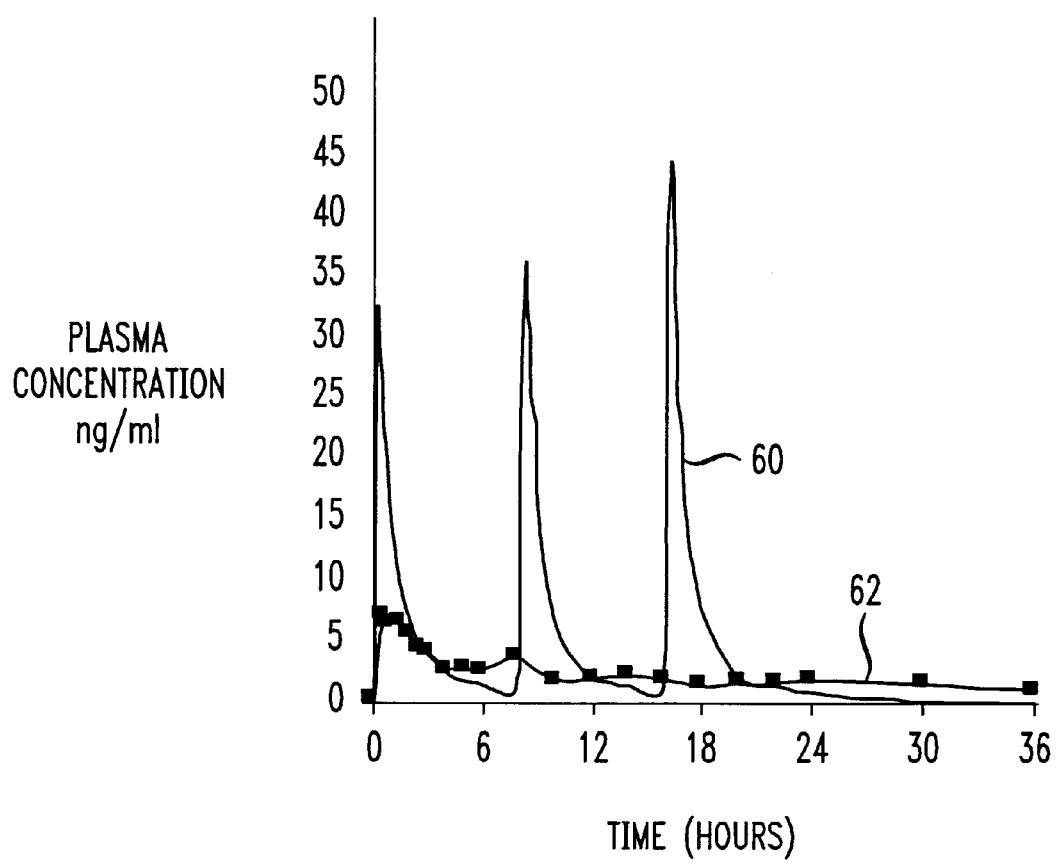
FIG. 12 depicts plasma levels of Drug A in pigs for a controlled release dosage form in accordance with the illustrative embodiment of the present invention and for an immediate release formulation.

FIG. 12 depicts the mean plasma levels following intraduodenal administration of the immediate release formulation and the controlled release dosage form. Plot 60 depicts the mean plasma levels following administration via the immediate release formulation and plot 62 depicts the mean plasma levels following administration via the controlled release dosage form.

FIG. 12 shows that the relative bioavailability of Drug A from the controlled dosage form (plot 62) was less than that from the immediate release solution (plot 60). But it can also be seen that Drug A, when administered via the controlled release dosage form, was released over an extended period of time and that as a consequence, absorption was prolonged and plasma levels remained elevated for over a twenty-four hour period. FIG. 12 also indicates that dose dumping did not occur. Greater than ninety percent of Drug A was release from the controlled release dosage form. Regarding the stability study, no degradation or change in dissolution was observed after three-month storage at 40° C. and 75 percent relative humidity.

The above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references referred to herein, including patents, patent applications, and publications, are incorporated herein by reference.

We claim:

1. A dosage form for controlled release of a drug, the dosage form comprising:
   a stack having a first end and a second end, wherein said stack comprises:
      a plurality of dose units, wherein each dose unit is characterized by a rate of dissolution; and a plurality of separators, wherein said separators decrease said rate of dissolution of said dose units, wherein, within said stack, proximate dose units are separated by one of said separators; and a housing that encases said stack, wherein said housing has a physical adaptation that provides access to said second end of said stack; and said separators are dissolved in-situ within said housing.

2. The dosage form of claim 1 wherein one of said dose units is disposed at said second end of said stack.

3. The dosage form of claim 2 wherein said physical adaptation comprises a rapidly-dissolvable material, wherein a portion of said housing that is disposed proximal to said second end of said stack comprises said rapidly-dissolvable material.

4. The dosage form of claim 2 wherein said physical adaptation comprises a permeable material, wherein a portion of said housing that is disposed proximal to said second end of said stack comprises said permeable material.

5. The dosage form of claim 1 wherein said said physical adaptation comprises an opening, wherein a portion of said housing that is disposed proximal to said second end of said stack is open to said stack, and wherein one of said separators is disposed at said second end of said stack.

6. The dosage form of claim 1 wherein each separator seals to said housing.

7. The dosage form of claim 1 wherein said separators have a hemispherical shape and are suitably sized to nest with each other.

8. The dosage form of claim 1 further comprising an immediate release component.

9. The dosage form of claim 1 further comprising spacers, wherein said spacers provide structural support for said separators.

10. The dosage form of claim 9 wherein said spacers are configured as annular rings.

11. The dosage form of claim 1 wherein a first separator of said plurality thereof has a first rate of dissolution and a second separator of said plurality thereof has a second rate of dissolution, wherein said first rate of dissolution is different than said second rate of dissolution.

12. The dosage form of claim 11 wherein said first separator has a first thickness and said separator has a second thickness and said first thickness is different from said second thickness.

13. The dosage form of claim 11 wherein said first separator comprises a first material and said second separator comprises a second material and said first material is different from said second material.

14. The dosage form of claim 1 wherein said separators dissolve at a rate that is suitable for releasing drug from one of said dose units at a frequency that is in a range of about once per hour to about once per twelve hours.

15. The dosage form of claim 1 wherein said separators dissolve at a rate that is suitable for releasing drug from one of said dose units at a frequency that is in a range of about once per two hours to about once per six hours.

16. The dosage form of claim 1 wherein at least one of said dose units comprises:

a substrate;

a cover, wherein said cover is attached to said substrate; and an amount of drug, wherein said drug is enclosed between said substrate and said cover.

17. The dosage form of claim 16 wherein said one dose unit comprises drug that is electrostatically deposited on said substrate.

18. The dosage form of claim 16 further comprising a dissolution-enhancing amount of a surfactant, wherein said surfactant is incorporated in or on at least one of said substrate and said cover.

19. The dosage form of claim 1 wherein at least one of said dose units differs from other of said dose units by a parameter selected from the group consisting of type of drug and amount of drug.

20. The dosage form of claim 1 further comprising a dissolution-enhancing amount of a surfactant, wherein said surfactant is incorporated in or on said separators.

21. A dosage form comprising:

an immediate-release section, wherein said immediate-release section consists of a first dose unit, and wherein said immediate-release section releases drug from said first dose unit in a first period of time; and an extended-release section that is adjacent to said immediate-release section, wherein said extended-release section comprises:

a separator, wherein said separator is proximate to said immediate-release section;

a second dose unit, wherein said second dose unit is adjacent said separator and distal to said immediate-release section; and water-impermeable wall, wherein said wall encases said second dose unit and a portion of said separator so that drug cannot be released from said second dose unit until said separator dissolves, and wherein said separator dissolves in-situ within said wall;

wherein said extended-release section releases drug from said second dose unit in a second period of time that is longer than said first period of time.

22. A method comprising:

arranging a plurality of dose units and a plurality of separators in alternating fashion so that proximate dose units are separated by a separator; and encapsulating said dose units and said separators in a housing, wherein said housing is physically adapted to controllably admit fluid proximal to an end of said plurality of alternately arranged dose units and separators.

23. The method of claim 22 wherein said separators have a hemispherical shape.

24. The method of claim 22 wherein the operation of arranging further comprises disposing a spacer between proximate separators.

25. The method of claim 22 wherein said housing has a cylindrical shape and wherein fluid is admitted at one end of said housing.

* * * * *